United States Patent [19]
Tomaru et al.

[11] Patent Number: 5,977,413
[45] Date of Patent: Nov. 2, 1999

[54] METHOD FOR PRODUCING BIS(3-AMINO-4-HYDROXYPHENYL) COMPOUNDS

[75] Inventors: Jun-ichiro Tomaru, Okegawa; Kenji Kunikata; Masaki Fujimoto, both of Omiya, all of Japan

[73] Assignee: Nippon Kayaku Kabushiki Kaisha, Tokyo, Japan

[21] Appl. No.: 09/124,202

[22] Filed: Jul. 28, 1998

[30] Foreign Application Priority Data

Aug. 4, 1997 [JP] Japan ................................. 9-221181

[51] Int. Cl.$^6$ .................................................. C07C 209/36
[52] U.S. Cl. .......................... 564/423; 564/418; 564/366; 564/430; 564/315
[58] Field of Search ..................... 564/315, 430, 564/366, 418, 423, 422

[56] References Cited

FOREIGN PATENT DOCUMENTS 6-211752  8/1994  Japan .

OTHER PUBLICATIONS

CA:95:186744 abs of Synthesis, by Ayyangar 8 pp. 640–3, 1981.

CA:120:244694 abs of JP05310698, 1992.

CA:67:21604 abs of GB1047607, 1966.

CA:80:145765 abs of SU420617, 1972.

*Primary Examiner*—Gary Geist
*Assistant Examiner*—Jean F Vollano
*Attorney, Agent, or Firm*—Nields, Lemack & Dingman

[57] ABSTRACT

Disclosed is a method for producing bis(3-amino-4-hydroxyphenyl) compounds, which comprises reducing bis (3-nitro-4-hydroxyphenyl) compounds with hydrazines in the presence of a catalyst. The method produces bis(3-amino-4-hydroxyphenyl) compounds of high quality under mild conditions at high yields. The products can be isolated and purified in a simple manner to have a higher purity. The method is suitable to industrial-scale production of the products.

3 Claims, No Drawings

METHOD FOR PRODUCING BIS(3-AMINO-4-HYDROXYPHENYL) COMPOUNDS

FIELD OF THE INVENTION

The present invention relates to a method for producing bis(3-amino-4-hydroxyphenyl) compounds.

BACKGROUND OF THE INVENTION

At present, bis(3-amino-4-hydroxyphenyl) compounds, especially 2,2-bis(3-amino-4-hydroxyphenyl) hexafluoropropane are important as materials for producing heat-resistant polymers, etc. A method mentioned below is known for producing bis(3-amino-4-hydroxyphenyl) compounds, which, however, is problematic in the following points. Japanese Patent Application Laid-Open (JP-A) No. Hei-6-211752 discloses a method of catalytic hydrogenation reduction of bis(3-nitro-4-hydroxyphenyl) hexafluoropropane with a catalyst of palladium-carbon under high-pressure hydrogen. In this method, the purity of 2,2-bis(3-amino-4-hydroxyphenyl)hexafluoropropane produced in the reaction mixture is 97%, and after the catalyst is removed through filtration, the mixture is poured into water for crystallization to obtain a dark gray product. This is recrystallized from a mixture of ethyl acetate and n-hexane to obtain the intended product, 2,2-bis(3-amino-4-hydroxyphenyl)hexafluoropropane. In this method, the starting compound is catalytically reduced with high-pressure hydrogen at a high temperature, and the method requires a pressure reactor (e.g., autoclave). Therefore, the method could neither be economical nor advantageous in view of the complicated operations it requires. In addition, the crude product obtained in the method contains coloring components that are difficult to remove, which brings about another problem that the post treatment of the product is not easy.

The problems with the conventional method for producing bis(3-amino-4-hydroxyphenyl) compounds noted above are that the method requires severe reaction conditions, expensive equipment and complicated operations, and is therefore neither economical nor simple, that the removal of impurities such as coloring components from the crude product obtained requires specific purification, and that the yield of the product is low.

SUMMARY OF THE INVENTION

We, the present inventors have assiduously studied so as to solve the problems with the conventional method noted above, and, as a result, have found that, when bis(3-nitro-4-hydroxyphenyl) compounds are reduced with hydrazines in the presence of a catalyst, then bis(3-amino-4-hydroxyphenyl) compounds of high purity are produced under mild reaction conditions at high yields. On the basis of this finding, we have completed the present invention.

Specifically, the invention provides the following:

(1) A method for producing bis(3-amino-4-hydroxyphenyl) compounds, which comprises reducing bis(3-nitro-4-hydroxyphenyl) compounds with hydrazines in the presence of a catalyst.

(2) The method for producing bis(3-amino-4-hydroxyphenyl) compounds according to (1), wherein the bis(3-nitro-4-hydroxyphenyl) compounds are those of a formula (1):

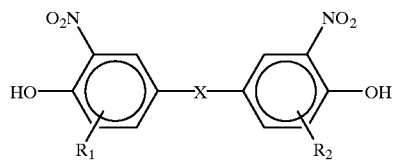

where X represents a methylene, substituted alkylene, aralkylene, oxy, thio, sulfoxide, sulfone, carbonyl or amino group, or a direct bond between the phenyl groups;

$R_1$ and $R_2$ each represent a hydrogen atom, an alkyl group, an alkoxy group, a hydroxyl group, an acyl group, an alkyloxycarbonyl group, a carbamoyl group, an acyloxy group, or a halogen atom, and $R_1$ and $R_2$ may be the same or different, and the bis(3-amino-4-hydroxyphenyl) compounds are those of a formula (2):

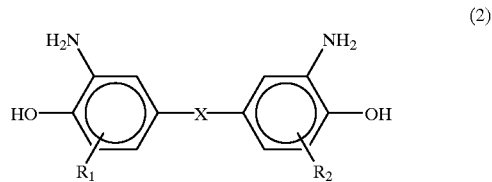

where X, $R_1$ and $R_2$ have the same meanings as above.

(3) The method for producing bis(3-amino-4-hydroxyphenyl) compounds according to (2), wherein X is a substituted alkylene group.

(4) The method for producing bis(3-amino-4-hydroxyphenyl) compounds according to (3), wherein the substituted alkylene is 1,1,1,3,3,3-hexafluoropropylene.

(5) The method for producing bis(3-amino-4-hydroxyphenyl) compounds according to (1), wherein the catalyst is a combination of an iron salt and active charcoal.

(6) The method for producing bis(3-amino-4-hydroxyphenyl) compounds according to (1), wherein the catalyst is a nickel catalyst or a noble metal catalyst.

(7) The method for producing bis(3-amino-4-hydroxyphenyl) compounds according to (6), wherein the noble metal catalyst is a platinum and/or palladium catalyst as dispersed on a supporting substance.

(8) The method for producing bis(3-amino-4-hydroxyphenyl) compounds according to any one of (1) to (7), wherein the reduction is effected in any of lower aliphatic alcohols having from 1 to 4 carbon atoms, lower diols, cyclic ethers or acyclic ethers.

(9) The method for producing bis(3-amino-4-hydroxyphenyl) compounds according to any one of (1) to (8), wherein the reaction temperature falls between 0 and 120° C.

DETAILED DESCRIPTION OF THE INVENTION

Now, the method of the invention is described in detail hereinunder.

Bis(3-nitro-4-hydroxyphenyl) compounds which are the starting compounds in the method of the invention are not specifically limitative, provided that they have two 3-nitro- 4-hydroxyphenyl groups as bonding to each other either directly or via a linking group. The linking group is not also specifically limitative, provided that it is a divalent atom or group via which the two 3-nitro-4-hydroxyphenyl groups bond to each other. It includes, for example, divalent atoms such as an oxygen atom, a substituted or unsubstituted nitrogen atom, a substituted or unsubstituted sulfur atom, a substituted or unsubstituted carbon atom or the like; divalent hydrocarbon residues having from 1 to 10 or so carbon atoms, which may be substituted or unsubstituted and/or may optionally have hetero atoms in the linking moiety; and divalent groups composed of any of those divalent atoms and hydrocarbon residues. Specific examples of bis(3-nitro-4-hydroxyphenyl) compounds that have two 3-nitro-4-hydroxyphenyl groups as bonding to each other via or not via any of those linking groups include the compounds of formula (1) noted above.

In formula (1), X includes, for example, divalent linking groups of the following formulae:

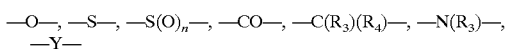

wherein n represents an integer of from 1 to 2;

$R_3$ and $R_4$ may be the same or different, and each independently represents a hydrogen atom, or a substituted or unsubstituted hydrocarbon atoms having from 1 to 10, but preferably from 1 to 6 carbon atoms;

Y represents a divalent, substituted or unsubstituted, and/or optionally hetero atom-interrupted polymethylene chain, or a divalent cyclic group.

As one example of the hydrocarbon residue for $R_3$ and $R_4$, mentioned is a substituted or unsubstituted alkyl group, which includes, for example, methyl, ethyl, n-propyl, isopropyl, n-butyl, isobutyl, tert-butyl, n-pentyl, isopentyl, n-hexyl, h-heptyl, n-octyl, 2-ethylhexyl, 2-ethyldecyl, n-decyl and n-dodecyl groups. The substituents for the groups include a halogen atom, an amino group, a hydroxyl group, etc. The substituted alkyl group includes, for example, chloromethyl, fluoromethyl and trifluoromethyl groups. The hydrocarbon residue for $R_3$ and $R_4$ may also be a cyclic group such as a phenyl group or the like.

Specific examples of the linking group X include methylene, 2,2-propylene, 1,1,1,3,3,3-hexafluoropropylene, 3,3-pentylidene, benzylidene, oxy, thio, sulfoxido, sulfone, carbonyl, amino, methylamino, ethylamino and anilino groups, and a direct bond between the phenyl groups.

The alkyl group for $R_1$ and $R_2$ in formula (1) may have from 1 to 20, but preferably from 1 to 10 carbon atoms. More preferably, it is a lower alkyl group having from 1 to 6 carbon atoms. Specific examples of the alkyl group include methyl, ethyl, n-propyl, isopropyl, n-butyl, isobutyl, tert-butyl, n-pentyl, isopentyl, n-hexyl, n-heptyl, n-octyl, 2-ethylhexyl, 2-ethyldecyl, n-decyl and n-dodecyl groups. The alkoxy group for those may have from 1 to 20, but preferably from 1 to 10 carbon atoms. More preferably, it is a lower alkoxy group having from 1 to 6 carbon atoms. Specific examples of the alkoxy group include methoxy, ethoxy, n-propoxy, isopropoxy, n-butoxy, isobutoxy, tert-butoxy, pentyloxy, hexyloxy, octyloxy, 2-ethylhexyloxy, decyloxy and dodecyloxy groups. The acyl group may have from 1 to 20, but preferably from 1 to 10 carbon atoms. More preferably, it is a lower acyl group having from 1 to 6 carbon atoms. Specific examples of the acyl group include acetyl, propanoyl, butanoyl, pentanoyl, hexanoyl, heptanoyl and octanoyl groups. As the alkyl moiety in the alkyloxycarbonyl group, referred to is the alkyl group noted above.

Specific examples of the alkyloxycarbonyl group include methylcarboxylate, ethylcarboxylate, propylcarboxylate, butylcarboxylate, pentylcarboxylate, hexylcarboxylate and 2-ethylhexylcarboxylate groups. Specific examples of the carbamoyl group include residues of carboxamides and lower alkyl derivatives thereof such as carboxylic acid-mono- or di-loweralkylamide, for example, carboxylic acid dimethylamides, carboxylic acid diethylamides, carboxylic acid methylamides and carboxylic acid ethylamides. As the acyl moiety in the acyloxy group, referred to is the acyl group noted above. Specific examples of the acyloxy group include acetoxy, propionyloxy and butyryloxy groups. Specific examples of the halogen atom for $R_1$ and $R_2$ include fluorine, chlorine, bromine and iodine atoms.

As bis(3-nitro-4-hydroxyphenyl) compounds of formula (1), for example, mentioned are bis(3-nitro-4-hydroxyphenyl)methanes, 2,2-bis(3-nitro-4-hydroxyphenyl)propanes, 2,2-bis(3-nitro-4-hydroxyphenyl)hexafluoropropanes, 3,3-bis(3-nitro-4-hydroxyphenyl)pentanes, 2,2'-dinitro-4,4'-benzylidene-bisphenols, bis(3-nitro-4-hydroxyphenyl) ethers, bis(3-nitro-4-hydroxyphenyl)sulfides, bis(3-nitro-4-hydroxy phenyl) sulfones, bis(3-nitro-4-hydroxyphenyl)sulfoxides, bis(3-nitro-4-hydroxyphenyl) ketones, bis(3-nitro-4-hydroxy phenyl)amines, and 3,3'-dinitrobiphenols, etc.

Specific examples of those bis(3-nitro-4-hydroxyphenyl) compounds include bis(3-nitro-4-hydroxyphenyl)methane, bis(3-nitro-4-hydroxy-5-ethoxyphenyl)methane, bis(3-nitro-4-hydroxy-5-acetoxyphenyl)methane, bis(3-nitro-4-hydroxy-5-(N,N-diethylamido)phenyl)methane, bis(3-nitro-4-hydroxy-6-fluorophenyl)methane, 2,2-bis(3-nitro-4-hydroxy phenyl)hexafluoropropane, 2,2-bis(3-nitro-4-hydroxy-5-methylphenyl)hexafluoropropane, 2,2-bis(3-nitro-4-hydroxy-5-hydroxyphenyl)hexafluoropropane, 2,2-bis(3-nitro-4-hydroxy-6-propanoylphenyl)hexafluoropropane, 2,2-bis(3-nitro-4-hydroxy-5-butylcarboxyphenyl)hexafluoropropane, 2,2-bis(3-nitro-4-hydroxy-6-chlorophenyl)hexafluoropropane, 3,3-bis(3-nitro-4-hydroxyphenyl)pentane, 3,3-bis(3-nitro-4-hydroxy-5-isopropylphenyl)pentane, 3,3-bis(3-nitro-4-hydroxy-5-chlorophenyl)pentane, 2,2'-dinitro-4,4'-benzylidene-bisphenol, 2,2'-dinitro-4,4'-benzylidene-6,6'-dimethylbisphenol, 2,2'-dinitro-4,4'-benzylidene-6,6'-dichlorobisphenol, bis(3-nitro-4-hydroxyphenyl) ether, bis(3-nitro-4-hydroxy-5-methylphenyl) ether, bis(3-nitro-4-hydroxy-5-butylcarboxyphenyl) ether, bis(3-nitro-4-hydroxy-6-chlorophenyl) ether, bis(3-nitro-4-hydroxyphenyl)sulfide, bis(3-nitro-4-hydroxy-5-methylphenyl)sulfide, bis(3-nitro-4-hydroxy-6-propanoylphenyl)sulfide, bis(3-nitro-4-hydroxy-5-bromophenyl)sulfide, bis(3-nitro-4-hydroxyphenyl)sulfone, bis(3-nitro-4-hydroxy-5-methylphenyl)sulfone, bis(3-nitro-4-hydroxy-6-propanoylphenyl)sulfone, bis(3-nitro-4-hydroxy-6-methylphenyl) ketone, bis(3-nitro-4-hydroxy-5-ethoxyphenyl) ketone, bis(3-nitro-4-hydroxy-5-isopropylphenyl) ketone, bis(3-nitro-4-hydroxy-6-methylphenyl) ketone, bis(3-nitro-4-hydroxyphenyl)amine, bis(3-nitro-4-hydroxy-5-methylphenyl)amine, bis(3-nitro-4-hydroxy-5-methoxyphenyl)amine, N,N-di(3-nitro-4-hydroxyphenyl)aniline, 3,3'-dinitro-4,4'-dihydroxydiphenyl, 3,3'-dinitro-4,4'-dihydroxy-5,5'-dimethyldiphenyl, 3,3'-dinitro-4,4'-dihydroxy-5,5'-dichloro diphenyl, etc., which, however, are not limitative.

Hydrazines which are used as a reducing agent in the invention may be any of hydrazine and its derivatives, such as $C_{1-6}$ hydrocarbon-substituted hydrazines, and even their salts, so far as they have reducing capabilities. For example, employable are hydrazine, hydrazine monohydrate, lower alkylhydrazines such as methylhydrazine, and also hydrazinium salts such as hydrazinium chloride and hydrazinium sulfate. These reducing agents can be used in the form of their solutions, such as aqueous solutions, alcoholic solutions or etheric solutions. Preferred are aqueous solutions of 60 to 80 wt. % hydrazine monohydrate. Hydrazines are used in an amount of from 2.0 to 20.0 mols, preferably from 2.5 to 10.0 mols, more preferably from 3.0 to 5.0 mols, per mol of bis(3-nitro-4-hydroxyphenyl) compounds.

The catalyst for use in the invention may be a combination of an iron salt and active charcoal, or a nickel or noble metal catalyst.

As the iron salt, preferred are iron halides, which include, for example, hydrates or anhydrides of ferrous chloride, ferric chloride, ferrous bromide or ferric bromide. The amount of the iron salt to be used may be from 0.01 to 0.5 mols, preferably from 0.02 to 0.1 mols, per mol of bis(3-nitro-4-hydroxyphenyl) compounds. The active charcoal to be combined with the iron salt may be either wetted or dried. Its amount may be from 1 to 100 parts by weight, preferably from 5 to 10 parts by weight, relative to 100 parts by weight of bis(3-nitro-4-hydroxyphenyl) compounds.

The nickel catalyst for use in the invention may be either one as carried by a carrier, or Raney nickel, but preferred is Raney nickel. Regarding the ratio by weight of Raney nickel to the starting aromatic-dinitro compounds, it is desirable that the amount of Raney nickel is from 0.1 to 50.0% by weight, preferably from 1.0 to 10.0% by weight, based on the bis(3-nitro-4-hydroxyphenyl) compounds.

The noble metal catalyst for use in the invention includes platinum, palladium, ruthenium, etc., which may be dispersed on a support such as active charcoal, silica gel, alumina, barium sulfate, calcium carbonate, porous diatomaceous earth, zirconia, magnesium oxide or the like. Especially preferably, it is dispersed on active charcoal and/or alumina and/or silica gel and is carried by them. In one preferred embodiment, from 0.1 to 20.0% by weight, more preferably from 1.0 to 5.0% by weight of palladium, based on the support substance, is carried by active charcoal, and the thus-carried palladium catalyst is used. The noble metal may also be used in the form of its oxide, which includes, for example, platinum oxide and palladium oxide.

Regarding the ratio by weight of the noble metal catalyst to the starting dinitro-aromatic compounds, it is desirable that the amount of the noble metal to be used is from 0.01 to 20.0% by weight, preferably from 0.01 to 5.0% by weight, most preferably from 0.05 to 0.5% by weight, based on the bis(3-nitro-4-hydroxyphenyl) compounds. The catalyst may be a fresh one or a recovered or recycled one.

In the method of the invention, the reduction may be effected generally in a solvent. For this, organic solvents may be employed, which include, for example, lower aliphatic alcohols having from 1 to 4 carbon atoms, such as methanol, ethanol, isopropanol, etc.; lower diols such as ethylene glycol, propylene glycol, diethylene glycol, etc.; cyclic ethers such as dioxane, tetrahydrofuran, etc.; acyclic ethers such as ethylene glycol ether, etc.; and mixed solvents comprising any of those organic solvents and water. Especially preferred are methanol, isopropanol and tetrahydrofuran. The amount of the solvent, if used, may be from 0.1 to 20.0 parts by volume, preferably from 0.5 to 5.0 parts by volume, relative to one part by weight of bis(3-nitro-4-hydroxyphenyl) compounds. The water content of the mixed solvent comprising the organic solvent and water may be from 1.0 to 99.0% by volume, preferably from 5.0 to 50.0% by volume.

In the method of the invention, the reaction temperature in the reduction may fall generally between 0 and 120° C., preferably between 10 and 100° C., more preferably between 10 and 90° C., and even more preferably between 40 and 70° C.

In the method of the invention, the means of processing the reactants is not specifically limitative. In general, a bis(3-nitro-4-hydroxyphenyl) compound is dissolved in a lower aliphatic alcohol such as methanol or the like, or is directly stirred in dispersion, and thereafter mixed with a predetermined amount of a catalyst. Next, the resulting mixture is kept at a predetermined temperature, to which is gradually and dropwise added a predetermined amount of a hydrazine compound, for example, an aqueous solution of 60 wt. % hydrazine monohydrate. Alternatively, a predetermined amount of a hydrazine compound is first put into a reactor and kept at a predetermined temperature, and a bis(3-nitro-4-hydroxyphenyl) compound is, after having been dissolved or dispersed in a reaction solvent or while being in powder, continuously or intermittently added to the reactor and is reacted with the hydrazine compound. Though depending on the amount of the catalyst used and the reaction temperature, the reducing agent and the bis(3-nitro-4-hydroxyphenyl) compound are added to the reactor generally over a period of from 5 minutes to 12 hours. After the reducing agent and the bis(3-nitro-4-hydroxyphenyl) compound are added, the resulting mixture is, if desired, stirred for further 5 minutes to 48 hours, preferably for further 30 minutes to 12 hours.

Where the product formed is sensitive to oxidation, the reaction is preferably effected in an atmosphere of protective vapor, for example, in a nitrogen atmosphere.

Where the product is easily colored by oxidation, an antioxidant such as hydrosulfide, sodium sulfide, hydroquinone, methoquinone or the like may be previously added to the reaction system, if desired. The amount of the antioxidant, if added, may be from 0.001 to 0.5 parts by weight, but preferably from 0.01 to 0.1 parts by weight, relative to 1 part by weight of bis(3-nitro-4-hydroxyphenyl) compounds.

After the reaction, the product formed may be isolated from the reaction mixture in any ordinary method that is generally employed for isolating products from reaction mixtures. In general, in the invention, the catalyst used is removed from the reaction mixture through filtration or precipitation, then the reaction mixture is, after having been concentrated or without being concentrated, poured into a bad solvent, or a bad solvent is added to the optionally-concentrated reaction mixture, thereby making crystal precipitated, and the resulting crystal of the intended product is taken out through filtration. Where the reaction mixture is concentrated, it may be from 0.3 to 2.5 times (w/v) or so relative to 1 part by weight of the product, bis(3-amino-4-hydroxyphenyl) compounds formed. Then, a bad solvent may be added to the thus-concentrated reaction mixture which is still hot, thereby making crystal precipitated, and this may be gradually cooled to make the crystal grow therein. The bad solvent may be added to the mixture at room temperature. After having been precipitated, the crystal is collected through filtration. The bad solvent employable herein includes, for example, water and organic hydrocarbon solvents. Examples of the organic hydrocarbon solvents include aromatic hydrocarbons such as toluene, xylene, mesitylene, etc.; and aliphatic hydrocarbons such as n-hexane, cyclohexane, n-heptane, n-octane, etc. Their mixed solvents are also employable.

From the reaction mixture from which the catalyst has been removed, the solvent may be evaporated out. In this case, a crude product may be recovered from the concentrate. If desired, the crude product may be purified. For the purification, for example, the concentrate may be subjected to recrystallization using lower aliphatic alcohols having from 1 to 4 carbon atoms (e.g., methanol, ethanol, n-propyl alcohol, isopropyl alcohol, n-butyl alcohol, etc.) or their mixed solvents. For the recrystallization, also employable are lower carboxylates (e.g., methyl acetate, ethyl acetate, propyl acetate, methyl propionate, ethyl propionate, propyl propionate, etc.), or their mixed solvents. As the lower aliphatic alcohols, preferred are methanol and isopropyl alcohol. More preferred is isopropyl alcohol. As the lower carboxylates, preferred are ethyl acetate and ethyl propionate. More preferred is ethyl acetate. The amount of the solvent of lower aliphatic alcohols or lower carboxylates to be used may be from 0.1 to 50.0 parts by volume, but preferably from 0.1 to 10.0 parts by volume, more preferably from 0.5 to 2.0 parts by volume, relative to 1 part by weight of the product, bis(3-amino-4-hydroxyphenyl) compound formed. If desired, the products, bis(3-amino-4-hydroxyphenyl) compounds obtained herein may be further purified to have a higher purity, for example, by a method of completely dissolving the products optionally under heat in solvents followed by gradually cooling the resulting solutions for crystallization, a method of putting the products into bad solvents such as those mentioned above to form crystal followed by collecting the crystal through filtration, or a method of stirring and dispersing the crude products in solvents such as those mentioned above followed by filtering the resulting dispersion to collect the purified products.

The amount of the lower aliphatic alcohols, the lower carboxylates and their mixed solvents with the organic hydrocarbon solvents or water, if used, may be from 0.5 to 30.0 parts by volume, preferably from 1.0 to 10.0 parts by volume, more preferably from 3.0 to 5.0 parts by volume, relative to 1 part by weight of the crude products, bis(3-amino-4-hydroxyphenyl) compounds. In the mixed solvents, the ratio of the bad solvent of organic hydrocarbons or water is preferably from 5.0 to 95.0% by volume, more preferably from 10.0 to 60.0% by volume. If desired, distillation may be employed for the purification. The purity of the product can be easily measured through liquid chromatography.

Now, the invention is described in more detail with reference to the following Examples, which, however, are not intended to restrict the scope of the invention.

EXAMPLE 1

15.0 g of 2,2-bis(3-nitro-4-hydroxyphenyl) hexafluoropropane and 50.0 cc of methanol were put into a 100-cc four-neck flask equipped with a thermometer, a Dimroth condenser and a stirrer, and stirred therein, to which was added 0.23 g (dry weight) of E196R/W5%Pd (trade name, 5% palladium-carbon catalyst, manufactured by Degussa Japan Co.). This was heated and kept at 60 to 65° C., to which was dropwise added 11.8 g of an aqueous solution of 60% hydrazine monohydrate over a period of 20 minutes. If desired, the reaction system was cooled, as generating heat during the reaction. After the aqueous hydrazine solution was added, the mixture was stirred at 70° C. for 30 minutes, and then gradually cooled to room temperature. After the catalyst was removed through filtration, methanol and water were evaporated out of the reaction mixture to obtain a crude product of 2,2-bis(3-amino-4-hydroxyphenyl)hexafluoropropane. The crude yield was 12.6 g (98%). The purity in liquid chromatography was 98.3% (area %).

12.6 g of the crude product, 2,2-bis(3-amino-4-hydroxyphenyl)hexafluoropropane obtained above, and 50.0 cc of isopropyl alcohol were put into a 100-cc four-neck flask equipped with a thermometer, a Dimroth condenser and a stirrer, and heated therein until they dissolved in reflux to give a uniform solution. Then, 40 cc of isopropyl alcohol was evaporated out of the solution to make crystal precipitated in the solution. This was stirred under reflux for further 15 minutes, to which was gradually added 30 cc of toluene. This was further stirred still under reflux for additional 15 minutes. Next, this was gradually cooled to room temperature, and stirred for 30 minutes with cooling with ice in water at 0 to 5° C. In that manner, crystal was fully precipitated, and then taken out through filtration. This was fully washed with 50 cc of a cold mixed solution of isopropyl alcohol (10% by volume) and toluene (90% by volume), and then fully dried. Thus was obtained white crystal of high purity. The yield in purification was 89.9%, and the yield of the pure product was 11.6 g. The purity in liquid chromatography was 99.9% (area %).

EXAMPLE 2

400.0 g of 2,2-bis(3-nitro-4-hydroxyphenyl) hexafluoropropane and 1200 cc of methanol were put into a 2000-cc four-neck flask equipped with a thermometer, a Dimroth condenser and a stirrer, and stirred therein, to which was added 9.0 g (dry weight) of E196R/W5%Pd. This was heated and kept at 60 to 65° C. with stirring, to which was dropwise added 313.2 g of an aqueous solution of 60% hydrazine monohydrate over a period of 4 hours. After the aqueous hydrazine solution was added, the mixture was stirred for further 30 minutes, and then gradually cooled to room temperature. After the catalyst was removed through filtration, the reaction mixture was concentrated to obtain a crude product of 2,2-bis(3-amino-4-hydroxyphenyl) hexafluoropropane. The crude yield was 336.8 g (98%). The purity in liquid chromatography was 97.9% (area %).

The crude product was purified from a mixed solvent of isopropyl alcohol and toluene in the same manner as in Example 1 to obtain white crystal of high purity. The yield in purification was 89.3%, and the yield of the pure product was 306.9 g. The purity in liquid chromatography was 99.9% (area %).

EXAMPLE 3

100.0 g of 2,2-bis(3-nitro-4-hydroxyphenyl) hexafluoropropane, 300 cc of methanol, and 5.0 g of developed NDT-90 (trade name, Raney nickel catalyst, manufactured by Kawaken Fine Chemical Co.) were put into a 500-cc four-neck flask equipped with a thermometer, a Dimroth condenser and a stirrer, and heated, with stirring, up to 60° C. to completely dissolve 2,2-bis(3-nitro-4-hydroxyphenyl)hexafluoropropane in the solvent. The resulting solution was kept at 60 to 65° C., to which was dropwise added 78.3 g of an aqueous solution of 60% hydrazine monohydrate over a period of 1 hour. After the aqueous hydrazine solution was added, the mixture was stirred for further 30 minutes, and then gradually cooled to room temperature. After the catalyst was removed through filtration, the reaction mixture was concentrated to obtain a crude product of 2,2-bis(3-amino-4-hydroxy-phenyl) hexafluoropropane. The crude yield was 82.5 g (96.0%). The purity in liquid chromatography was 96.5% (area %).

The crude product was purified from a mixed solvent of isopropyl alcohol and toluene in the same manner as in Example 1 to obtain white crystal of high purity. The yield in purification was 85.5%, and the yield of the pure product was 73.5 g. The purity in liquid chromatography was 99.9% (area %).

As has been mentioned in detail hereinabove, the method of the invention uses hydrazines as the reducing agent for producing bis(3-amino-4-hydroxyphenyl) compounds from bis(3-nitro-4-hydroxyphenyl) compounds. The method requires simple operations only, and produces bis(3-amino-4-hydroxyphenyl) compounds of high purity at high yields. Of the products, 2,2-bis(3-amino-4-hydroxyphenyl) hexafluoropropane is especially useful as a starting compound for heat-resistant polymers, especially for those for electronic materials.

While the invention has been described in detail and with reference to specific embodiments thereof, it will be apparent to one skilled in the art that various changes and modifications can be made therein without departing from the spirit and scope thereof.

What is claimed is:

1. A method for 2,2-bis(3-amino-4-hydroxyphenyl) 1,1,1,3,3,3-hexafluoropropane, which comprises reducing 2,2-bis(3-nitro-4-hydroxyphenyl) 1,1,1,3,3,3-hexafluoropropane with hydrazines in the presence of platinum and/or palladium catalyst.

2. The method for producing 2,2-bis(3-amino-4-hydroxyphenyl) 1,1,1,3,3,3-hexafluoropropane according to claim 1, wherein the reduction is carried out in one or more solvent(s) selected from the group consisting of lower aliphatic alcohols having from 1 to 4 carbon atoms, lower diols, cyclic ethers and acyclic ethers.

3. The method for producing 2,2-bis( 3-amino-4-hydroxyphenyl) 1,1,1,3,3,3-hexafluoropropane according to claim 1, wherein the reaction temperature falls between 0 and 120° C.

* * * * *